United States Patent [19]
Clemens et al.

[11] Patent Number: 4,717,382
[45] Date of Patent: Jan. 5, 1988

[54] NONINVASIVE APPARATUS FOR TREATING A SUCKING CHEST WOUND

[75] Inventors: R. Michael Clemens, Beltsville; Kenneth A. Zseltvay, Rockville, both of Md.

[73] Assignee: Emergency Management Products, Inc., Rockville, Md.

[21] Appl. No.: 826,225

[22] Filed: Feb. 5, 1986

Related U.S. Application Data

[63] Continuation-in-part of Ser. No. 724,820, Apr. 18, 1985, abandoned.

[51] Int. Cl.⁴ ............................................. A61M 1/00
[52] U.S. Cl. ................................... 604/122; 604/236
[58] Field of Search ............. 4/144.3; 609/19, 35, 609/49, 54, 73, 122, 131–133, 140, 141, 236, 237, 247, 289, 290, 312–314, 338, 353; 277/34, 34.3; 128/132 R, 760, DIG. 15; 604/73, 35, 122, 236, 247, 289, 314, 338

[56] References Cited

U.S. PATENT DOCUMENTS

| | | | |
|---|---|---|---|
| 2,765,790 | 10/1956 | Dickson | 604/338 |
| 3,042,041 | 7/1962 | Jascalevich | 128/276 |
| 3,486,504 | 12/1969 | Austin, Jr. | 128/260 |
| 3,587,570 | 6/1971 | Kilbey | 128/96 |
| 4,202,058 | 5/1980 | Anderson | 4/144.3 |
| 4,465,062 | 8/1984 | Versaggi et al. | 604/247 |

FOREIGN PATENT DOCUMENTS

| | | | |
|---|---|---|---|
| 619574 | 4/1927 | France | 604/313 |
| 958719 | 3/1950 | France | 604/313 |
| 1011535 | 4/1952 | France | 604/313 |
| 124875 | 5/1928 | Switzerland | 604/313 |
| 641061 | 8/1950 | United Kingdom | |

Primary Examiner—C. Fred Rosenbaum
Assistant Examiner—J. L. Kruter
Attorney, Agent, or Firm—Donald A. Kettlestrings

[57] ABSTRACT

A noninvasive apparatus for temporarily assisting in the treatment of a sucking chest wound wherein a dome-shaped element having a one-way valve therein or connected thereto is positioned over the wound and strapped in substantially fluid-tight relationship with the patient's body.

9 Claims, 6 Drawing Figures

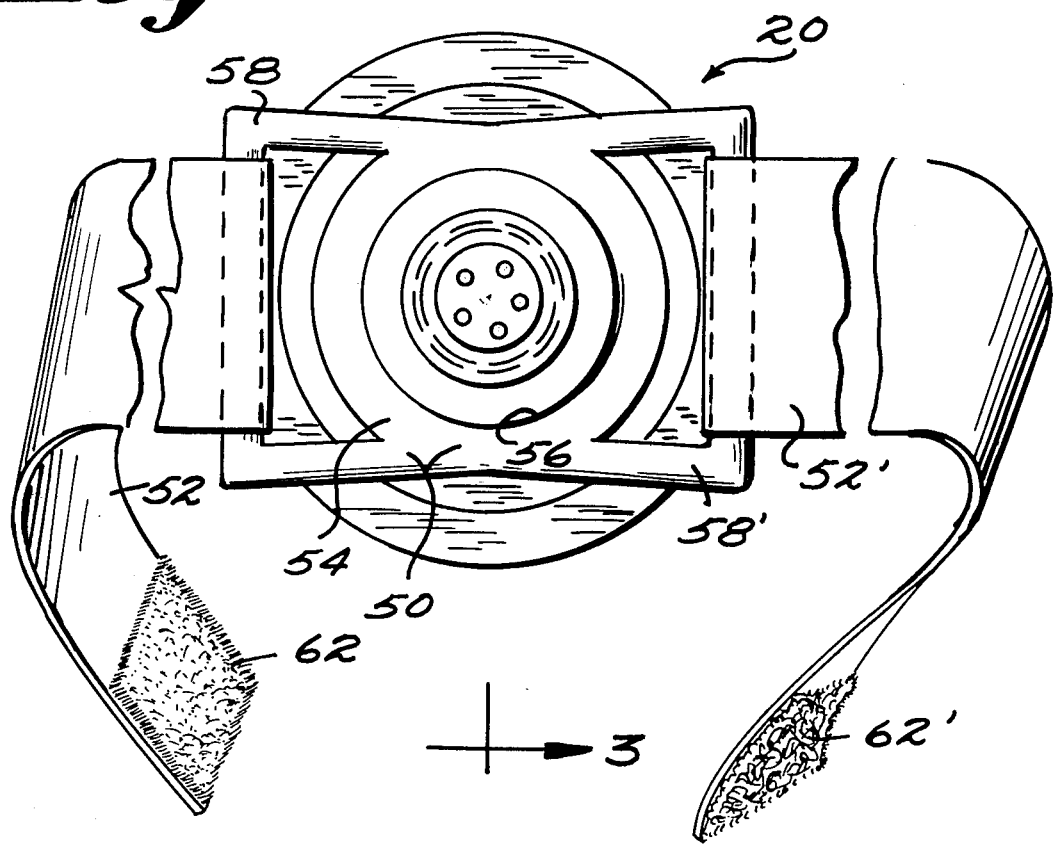
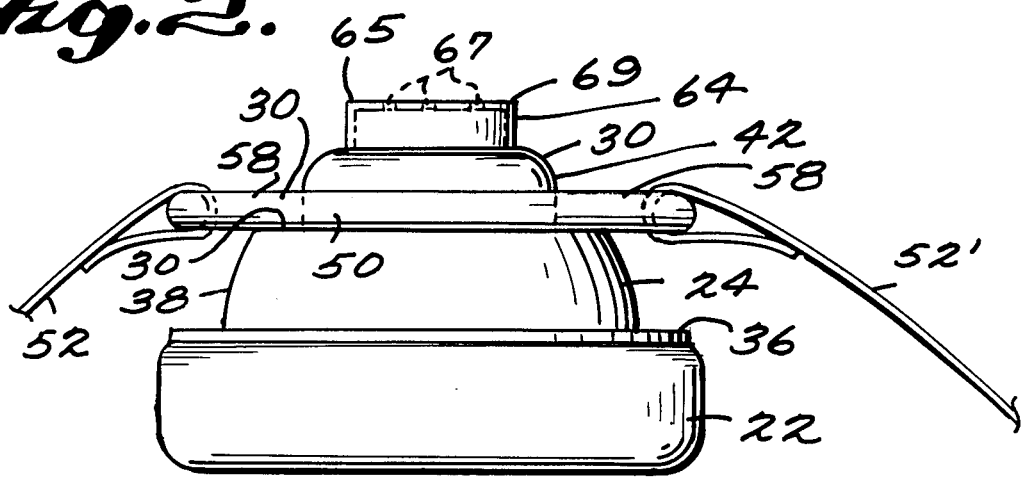
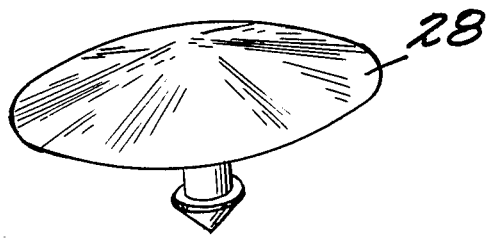

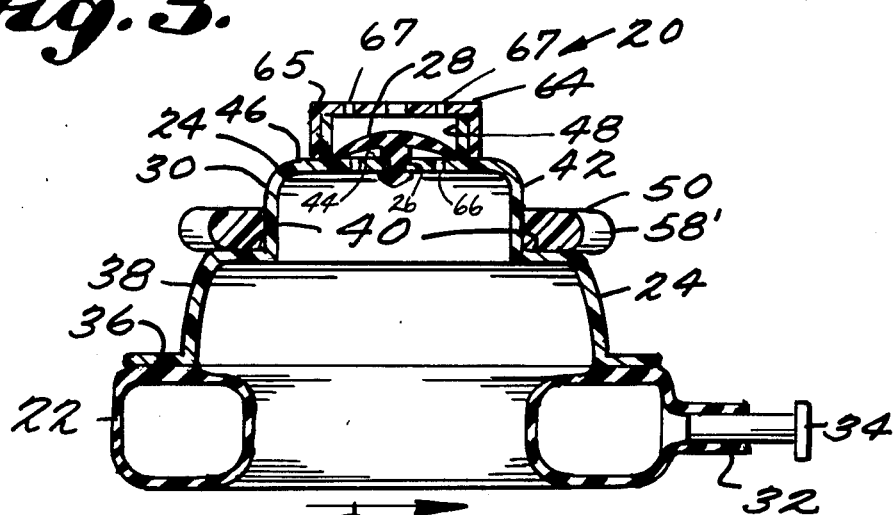
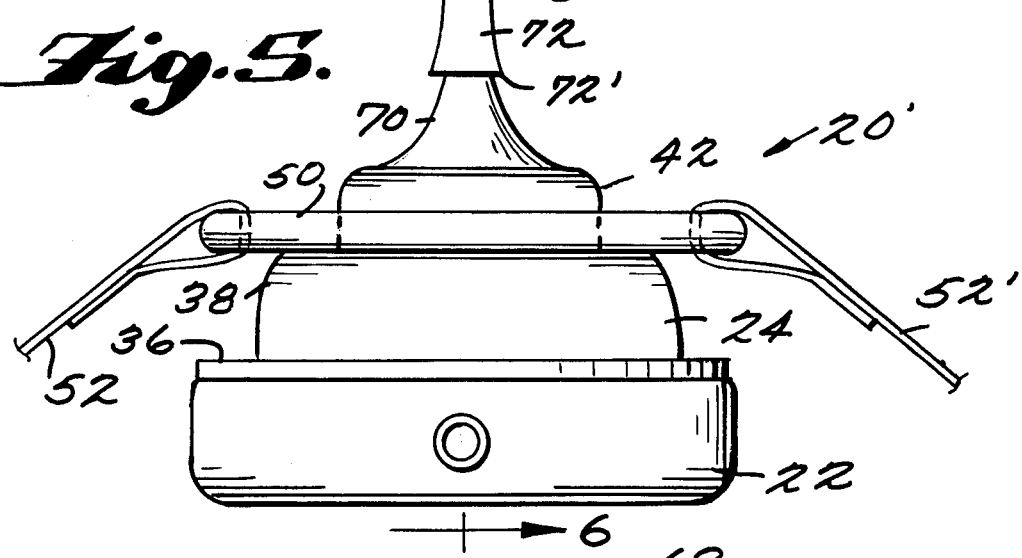
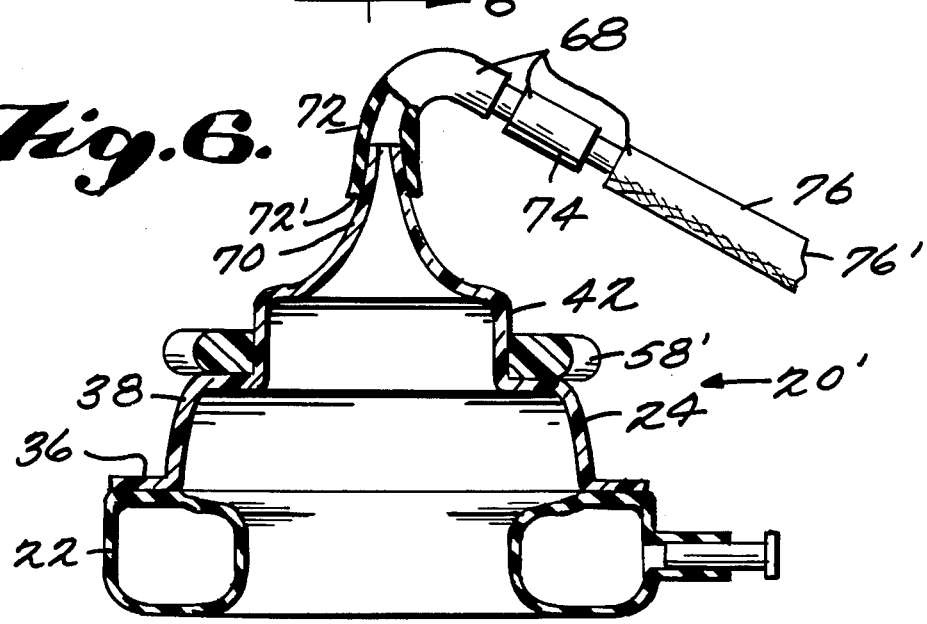

4,717,382

NONINVASIVE APPARATUS FOR TREATING A SUCKING CHEST WOUND

Cross Reference to Related Application

This application is a continuation-in-part of application Ser. No. 724,820, filed Apr. 18, 1985 now abandoned for Noninvasive Apparatus for Treating a Sucking Chest Wound.

BACKGROUND OF THE INVENTION

This invention relates to apparatus for temporarily assisting in treatment of a sucking chest wound and more particularly to noninvasive apparatus for sealing a sucking chest wound to reduce the possibility of development of a pneumothorax or a tension pneumothorax in the patient.

Current treatment for sucking chest wounds includes covering and sealing the wound with petroleum gauze, plastic or any occlusive dressing. This treatment may temporarily relieve the development of increased air pressure in the chest cavity, but if a lung has been punctured air will continue to flow into the pleural space. The increased air pressure in the chest cavity will impair the patient's ability to breathe until the pressure within the chest cavity is relieved by removing the dressing to allow the air to escape. The wound must then be resealed to once again prevent air from entering the wound from the outside.

Versaggi et al, U.S. Pat. No. 4,465,062 describes a noninvasive seal for a sucking chest wound, but the Versaggi device is not entirely satisfactory under all conditions of use. For example, the Versaggi valve is in close proximity to the wound, and fluid from the wound may interfere with operation of the valve. If an abundance of fluid collects in the valve of the Versaggi device the device may have to be removed from the patient to permit removal of the fluid from the valve. Because the Versaggi device relies on adhesive for creating a seal, the presence of fluid around the wound site may prevent the adhesive from creating the proper seal.

SUMMARY OF THE INVENTION

It is, therefore, an object of the present invention to provide a noninvasive apparatus for temporarily treating a sucking chest wound.

Another object is to provide such an apparatus which can be applied to the patient to provide the necessary fluid-tight seal between the apparatus and the patient, even with the presence of fluids around the wound site.

A further object of the invention is the provision of such an apparatus wherein its valve is positioned a considerable distance from the wound to prevent or reduce the possibility of fluid interfering with operation of the valve.

Still another object is to provide such an apparatus which is at least partially transparent to permit visualization of the wound and the interior of the apparatus during all medical procedures.

Yet another object of the present invention is the provision of such apparatus which is reusuable after proper cleaning and sterilization.

A still further object is to provide such an apparatus which can be strapped in a stable manner in substantially fluid-tight relationship against the patient's body and over the wound.

Additional objects and advantages of the invention will be set forth in part in the description which follows, and in part will be obvious from the description, or may be learned by practice of the invention. The objects and advantages are realized and attained by means of the instrumentalities and combinations particularly pointed out in the appended claims.

To achieve these and other objects the present invention provides a noninvasive apparatus for temporarily assisting in treatment of a sucking chest wound, the apparatus comprising: a flexible, annular member for placement in fluid-tight relationship against a patient's body and around the wound; normally empty, transparent, rigid, dome-shaped means attached in fluid-tight relationship to the annular member for enabling visual monitoring of fluid levels within the dome-shaped means, the dome-shaped means defining an aperture substantially at the apex of the dome-shaped means; valve means in operative relationship with the aperture for automatically enabling passage of air in substantially only one direction from within the dome-shaped means outwardly through the aperture and for permitting escape of air from the patient's thoracic cavity through the aperture while preventing air from entering the patient's thoracic cavity through the wound; and means integral with and in operative relationship with the rigid, dome-shaped means for enabling the adjustable strapping of the apparatus in a stable manner and in substantially fluid-tight relationship against the patient's body and over the wound. Preferably, screening means are provided in operative relationship with the valve means for protecting the valve means from objects and debris.

In an alternative embodiment of the invention, the valve means are part of a separate and conventional one-way valve assembly which can be selectively attached to the apparatus.

It is to be understood that both the foregoing general description and the following detailed description are exemplary and explanatory but are not restrictive of the invention.

BRIEF DESCRIPTION OF THE DRAWINGS

The accompanying drawings, which are incorporated in and constitute a part of this specification, illustrate examples of preferred embodiments of the invention and, together with the description, serve to explain the principles of the invention.

FIG. 1 is a top plan view of a preferred embodiment of the invention illustrating the strapping means in position for strapping the apparatus to the patient;

FIG. 2 is a side elevation view of the apparatus shown in FIG. 1;

FIG. 3 is a cross sectional view taken along the line 3—3 in FIG. 1 and looking in the direction of the arrows;

FIG. 4 is a perspective view of the valve of the apparatus;

FIG. 5 is a side elevation view of another embodiment of the invention and showing a conventional one-way valve assembly removably attached to the invention apparatus; and FIG. 6 is a cross sectional view of the apparatus taken along the line 6—6 in FIG. 5 and looking the direction of the arrows.

DESCRIPTION OF THE PREFERRED EMBODIMENTS

With reference to the drawings, wherein like reference characters designate like or corresponding parts throughout the several views, there is shown noninvasive apparatus 20 for temporarily assisting in treatment of a sucking chest wound. Apparatus 20 is comprised of a flexible, annular member 22 for placement in fluid-tight relationship against a patient's body and around the wound. Normally empty, transparent, rigid, dome-shaped means 24 are glued or otherwise conventionally attached in fluid-tight relationship to annular member 22 for enabling visual monitoring of the wound and of fluid levels within dome-shaped means 24. Dome-shaped means 24 further define an aperture 26 substantially at the apex of dome-shaped means 24, and valve means 28 are in operative relationship with aperture 26 for automatically enabling passage of air in substantially only one direction from within dome-shaped means 24 outwardly through aperture 26 and for permitting escape of air from the patient's thoracic cavity through aperture 26 while preventing air from entering the patient's thoracic cavity through the wound. Means 30, a portion of which is integral with dome shaped means 24, is also in operative relationship with rigid dome-shaped means 24 for enabling the adjustable strapping of apparatus 20 in a stable manner and in substantially fluid-tight relationship against the patient's body and over the wound.

Annular member 22 may be inflatable, and a flexible inflating stem 32 is provided with a stopper 34. Annular member 22 may also be comprised of a solid, flexible material or a porous may also be comprised of a solid, flexible material or a porous foam-like material. Silicon rubber has been found to be an appropriate material for annular member 22.

In accordance with one preferred embodiment of the invention, as shown in FIGS. 2-3, dome-shaped means 24 includes an annular flange 36 glued or otherwise conventionally attached in fluid-tight relationship to annular member 22. Dome-shaped means 24 further include a first annular sidewall 38 projecting upwardly from flange 36, an annular surface 40 projecting inwardly from sidewall 38 and substantially parallel with flange 36, a second annular sidewall 42 projecting upwardly from annular surface 40, a substantially flat element 44 defining at least one aperture 26 therein and connected to upper extremities 46 of sidewall 42 in substantially parallel relationship with annular surface 40, and a third annular sidewall 48 surrounding aperture 26 and projecting upwardly from flat element 44.

Valve means 28, in the embodiment of FIGS. 1-4, are in operative relationship with flat element 44 and with aperture 26 for automatically enabling passage of air in substantially only one direction from within dome-shaped means 24 outwardly through aperture 26 and for permitting escape of air from the patient's thoracic cavity while preventing air from entering the patient's thoracic cavity through the wound.

In the embodiment illustrated in FIGS. 1-4 strapping means 30 include a fastening member 50 shaped to fit over and slidably engage second annular sidewall 42 and to be positioned and held on annular surface 40. Straps 52, 52' are attached to fastening member 50 for holding fastening member 50 in position on annular surface 40 and for enabling the adjustable strapping of apparatus 20 in substantially fluid-tight relationship against the patient's body and over the wound.

In accordance with the invention, fastening member 50 defines a first annular element 54 defining an interior opening 56 of a size and shape to slidably engage second annular sidewall 42 when element 54 is positioned onto annular surface 40. First element 54 is also of a size and shape to enable element 54 to be positioned onto and supported by annular surface 40. Fastening member 50 also includes first and second strap-receiving elements 58, 58' projecting outwardly from first element 54, and straps 52, 52' are attached, respectively, to strap-receiving elements 58, 58'. Adjustable fastening means 62, 62' such as a buckle or Velcro, are provided in operative relationship with straps 52, 52' for adjustably connecting the straps together around the patient.

Screening means 64 are preferably provided in operative relationship with valve means 28 for protecting the valve means from objects and debris. In the preferred embodiment illustrated in FIGS. 1-4, screening means 64 include a cap-like element 65 which defines a plurality of openings 67. Upper portion 69 of element 65, is preferably, sized and shaped to allow a conventional medical adapter (not shown) to fit over and be attached to upper portion 69. This adapter can then be connected to conventional suction apparatus (not shown) to enable reduction of pressure within the thoracic cavity.

Dome-shaped means 24 are preferably comprised of a rigid acrylic plastic, such as acrylonitrile. An extrusion machine (not shown) can be used to form dome-shaped means 24 by squeezing melted plastic through a specially shaped die in a conventional manner.

In operation, a large area of the patient's chest surrounding the wound should be exposed. Apparatus 20 is then placed over the wound with annular member 22 positioned around the wound. If the wound is larger than the circumference of annular member 22, petroleum gauze (not shown) can be used to cover the edges of the wound to reduce the size of the opening, and apparatus 20 is then placed over the area where air appears to be entering the chest while overlapping onto the petroleum gauze.

Fastening member 50 is then placed over dome-shaped means 24, and first element 54 of fastening member 50 is slidably positioned around annular sidewall 42 and onto annular surface 40. Straps 52, 52' are then positioned around the patient, and adjustable fastening means 62, $\beta'$ such as Velcro or a buckle, are used to adjustably fasten the straps together and to force annular member 22 tightly against the patient's body around the wound and in substantially fluid-tight relationship with the patient's body.

With apparatus 20 in position over the wound, air will be permitted to escape from the thoracic cavity of the patient and air will be prevented from entering the thoracic cavity through the wound. As a result, a tension pneumothorax will be avoided.

Apparatus 20 is designed to prevent any part of the apparatus from contacting the wound. The location of valve 28 at the apex of dome-shaped means 24 permits the valve to be positioned a considerable distance above the wound and above the patient's skin. This reduces chances of any fluid interfering with operation of the valve, and the size of dome-shaped means 24 enables a substantial amount of fluid to collect within apparatus 20 before removal of the apparatus from the patient becomes necessary. If removal of apparatus 20 from the wound site becomes necessary, the apparatus can be reapplied and substantially fluid-tight contact between annular member 22 and the patient's body can be reestablished.

The flexibility of annular member 22 enables it to readily conform to the contours of the patient's body around the wound and also permits a substantially fluid-tight seal to be established between annular member 22 and the patient's body. Even if the patient is perspiring profusely or if the wound site is wet with blood or other fluids, the fluid-tight seal is maintained.

The transparency of rigid, dome-shaped means 24 enables visual monitoring of the wound during all medical procedures and permits visual monitoring of the interior of the apparatus and of the operation of valve 28. An umbrella valve 26 is preferably used in apparatus 20, and a plurality of additional apertures 66 are defined by flat element 44 and beneath the upper portion of umbrella valve 26. In this embodiment, air passes outwardly through additional apertures 66 as well as through aperture 26.

The structure of dome-shaped means 24 forming annular surface 40 and annular sidewall 42 in combination with fastening member 50 provides an extremely stable means for holding apparatus 20 against the patient's body without movement of apparatus 20 and without tipping thereof. It is important for apparatus 20 to be held against the patient in a firm and stable manner during use of apparatus 20. It is also desirable to have valve 28 positioned a significant distance from the wound to prevent or reduce the possibility of fluid interfering with operation of the valve. These objectives are best accomplished by providing for annular surface 40 to be located only a short distance above flange 36 so that fastening member 50 can be attached to dome-shaped means 24 only a short distance above annular member 22. This provides apparatus 20 with a significant amount of stability when in use, and apparatus 20 is not easily dislodged or tilted. Sidewall 42 provides the dual function of positioning valve 28 the desired distance from the wound while also providing, in combination with fastening member 50, an extremely stable means for holding apparatus 20 in position over the wound.

An alternative embodiment of the apparatus is illustrated in FIGS. 5-6 wherein a conventional one-way valve assembly 68 is used in combination with apparatus 20'. One example of an assembly 68 is described in U.S. Pat. No. 3,463,159. In the embodiment shown in FIGS. 5-6, no one-way valve is provided within dome-shaped means 24. Instead, valve assembly 68 is connected to dome-shaped means 24 by means of a hollow, tapered open-ended, nipple-like element 70 which is integral with and projects upwardly from the apex of dome-shaped means 24. As shown in FIG. 6, nipple-like element 70 defines a hollow interior in fluid communication with the interior of dome-shaped means 24 to enable selective attachment to element 70 of conventional assembly 68 in fluid communication with the interior of dome-shaped means 24. As shown in FIG. 6, a first flexible tube 72 is connected between nipple-like element 70 and conventional one-way valve 74, and a second flexible tube 76 is connected to an opposite end of valve 74.

In operation of the embodiment illustrated in FIGS. 5-6, assembly 68 is connected to apparatus 20 by forcing end 72' of tube 72 over nipple-like element 70. Apparatus 20' is strapped to the patient in the manner previously described. Air will then be permitted to escape from the patient's chest cavity and out through apparatus 20', tube 72, valve 74 and tube 76. Air will also be prevented from entering the chest cavity through the wound by the action of one-way valve 74. If desired, conventional suction apparatus (not shown) can be connected to the free end 76' of tube 76 to permit evacuation of air and/or other fluids from the chest cavity.

The invention in its broader aspects is not limited to the specific details shown and described, and departures may be made from such details without departing from the principles of the invention and without sacrificing its chief advantages.

What is claimed is:

1. A noninvasive apparatus for temporarily assisting in treatment of a sucking chest wond, said apparatus comprising:
   a flexible, annular member for placement in fluid-tight relationship against a patient's body and around said wound;
   transparent, rigid, dome-shaped means attached in fluid-tight relationship to said annular member for enabling visual monitoring of levels of fluids escaping from said wound and entering said apparatus beneath said dome-shaped means;
   said dome-shaped means including an annular flange attached in fluid-tight relationship to said annular member; a first annular sidewall projecting upwardly from said flange; an annular surface projecting inwardly from said sidewall and substantially parallel with said flange; a second annular sidewall projecting upwardly from said annular surface; a substantially flat element defining at least one aperture therein and connected to upper extremities of said second annular sidewall in substantially parallel relationship with said annular surface; and a third annular sidewall surrounding said aperture and projecting upwardly from said flat element;
   valve means in operative relationship with said flat element and said aperture for automatically enabling passage of air in substantially only one direction from within said dome-shaped means outwardly through said aperture and for permitting escape of air from the patient's thoracic cavity while preventing air from entering the patient's thoracic cavity through the wound;
   a fastening member shaped to fit over and slidably engage said second annular sidewall and to be positioned and held on said annular surface; and
   strapping means attached to said fastening member for holding said fastening member in position on said annular surface and for enabling the adjustable strapping of said apparatus in substantially fluid-tight relationship against the patient's body and over the wound.

2. Apparatus as in claim 6 wherein said flexible annular member is inflatable.

3. Apparatus as in claim 1 wherein said fastening-member comprises:
   a first element defining an interior opening of a size and shape to slidably engage said second annular sidewall when said first element is positioned onto said annular surface, said first element of a size and shape to enable said first element to be positioned onto and supported by said annular surface; and
   first and second strap-receiving elements projecting outwardly from said first element.

4. Apparatus as in claim 3 wherein said strapping means include straps attached to said strap-receiving elements; and adjustable fastening means in operative relationship with said straps for adjustably connecting said straps together around the patient.

5. Apparatus as in claim 1 further including screening means in operative relationship with said valve means for protecting said valve means from objects and debris.

6. A noninvasive apparatus for temporarily assisting in treatment of a sucking chest wound, said apparatus comprising:

a flexible, annular member for placement in fluid-tight relationship against a patient's body and around said wound;

transparent, rigid, dome-shaped means attached in fluid-tight relationship to said annular member for enabling visual monitoring of levels of fluids escaping from said wound and entering said apparatus beneath said dome-shaped means:

said dome-shaped means including an annular flange attached in fluid-tight relationship to said annular member; a first annular sidewall projecting upwardly from said flange; an annular surface projecting inwardly from said sidewall and substantially parallel with said flange; a second annular sidewall projecting upwardly from said annular surface: and an annular, tapered, open-ended, nipple-like element projecting upwardly from said second sidewall to enable selective attachment thereto of a conventional hollow medical adapter or tube in fluid communication with the interior of said dome-shaped means:

a fastening member shaped to fit over and slidably engage said second annular sidewall and to be positioned and held on said annular surface: and strapping means attached to said fastening member for holding said fastening member in position on said annular surface and for enabling the adjustable strapping of said apparatus in substantially fluid-tight relationship against the patient's body and over the wound.

7. Apparatus as in claim 6 wherein said flexible annular member is inflatable.

8. Apparatus as in claim 6 wherein said fastening member comprises:

a first element defining an interior opening of a size and shape to slidably engage said second annular sidewall when said first element is positioned onto said annular surface, said first element of a size and shape to enable said first element to be positioned onto and supported by said annular surface; and first and second strap-receiving elements projecting outwardly from said first element.

9. Apparatus as in claim 8 wherein said strapping means include straps attached to said strap-receiving elements; and adjustable fastening means in operative relationship with said straps for adjustably connecting said straps together around the patient.

* * * * *